United States Patent [19]

Kretschmer

[11] 4,022,578

[45] May 10, 1977

[54] DETECTOR TUBE

[75] Inventor: Wolfgang Kretschmer, Berlin, Germany

[73] Assignee: Auergesellschaft GmbH, Berlin, Germany

[22] Filed: May 5, 1976

[21] Appl. No.: 683,540

[30] Foreign Application Priority Data

Mar. 20, 1975 Germany .......................... 2512687

[52] U.S. Cl. ............................................. 23/254 R
[51] Int. Cl.² ................... G01N 21/12; G01N 31/22
[58] Field of Search .................. 23/254 R, 232 R

[56] References Cited

UNITED STATES PATENTS

| | | | |
|---|---|---|---|
| 2,487,077 | 11/1949 | Shepherd | 23/232 R |
| 2,593,878 | 4/1952 | Haines et al. | 23/254 R |
| 2,939,768 | 6/1960 | Grosskopf | 23/232 R |
| 3,355,251 | 11/1967 | McConnaughey | 23/232 R |
| 3,399,973 | 9/1968 | Grosskopf | 23/254 R |
| 3,437,448 | 4/1969 | Miczka | 23/254 R |

*Primary Examiner*—Robert M. Reese
*Attorney, Agent, or Firm*—Reed Smith Shaw & McClay

[57] ABSTRACT

A detector tube for detecting halogenated hydrocarbon compounds, preferably including first and second layers wherein the first layer comprises a carrier impregnated with hexavalent chromium and sulfuric acid to which is added an activator selected from the group consisting of 3-, 4-, and 5-valent compounds of nitrogen, 5- and 7-valent compounds of iodine and compounds of 4- and 6-valent selenium. A second layer for indicating the presence of a halogen or reaction product compound comprises a support material impregnated with a benzidine derivative, which may be positioned in a first tube with the first layer or in a second tube adapted for connection during detection with a first tube.

10 Claims, 3 Drawing Figures

FIRST LAYER
SILICA GEL IMPREGNATED WITH HEXAVALENT CHROMIUM, SULFURIC ACID & ACTIVATOR.

SECOND LAYER
SILICA GEL IMPREGNATED WITH BENZIDINE DERIVATIVE (FLOW OF AIR)

DETECTOR TUBE

FIELD OF THE INVENTION

The present invention relates to a detecting tube for the detection of halogenated hydrocarbon compound, and, in particular, to the detection of chlorine, bromine, and iodine derivatives of unsaturated hydrocarbons.

BACKGROUND OF THE INVENTION

Detection or testing tubes are old and well known. Detector tubes are used, for example, with a pump means to draw ambient air or other gases or vapors through the tube to provide a colorimetric indication of the presence of a selected compound. A detector tube typically comprises an elongated glass tube adapted to attach at its exhaust end to a pump for drawing gas through the tube from its other end comprising the intake port. Both ends are sealed to protect the active components contained therein prior to use. Each detector tube includes a colorimetric indicating material which is specific to a particular gas, vapor, mist or reaction product.

Detector tubes have been provided for the detection of halogenated hydrocarbon compounds and are also well known. These tubes comprise a first layer (in the direction of gas flow) in which the halogenated hydrocarbon is cracked (dissociated) and a second layer consisting of an indicator material to detect dissociated halogen or a reaction product from the first layer. For example, a substance based upon permanganate-sulfuric acid has been utilized in the first layer to achieve a cracking of the halogenated hydrocarbon compound. While this material provides initially satisfactory results, the permanganate is subject to a gradual decomposition with the associated formation of inactive tetravalent manganese lead which reduces the cracking power of the first layer so that the detection becomes insensitive to small concentrations, i.e., in the range of a few ppm. Moreover, decomposition of the permanganate can take place prior to the use of the detection tube resulting in a detection tube with little shelf life or stability.

Other materials have been used, such as an oxidizing medium consisting of a granular support carrier impregnated with a solution of sulfuric acid and chromium trioxide. While first layer based on hexavalent chromium associated with sulfuric acid are stable in storage, their capability to dissociate a halogenated hydrocarbon to attain the sensitivity necessary to indicate concentration ranges of a few parts per million is generally inadequate.

Accordingly, it is an object of the present invention to provide a material for use in the first layer of a detection tube which is stable during storage and which at the same time provides a high degree of sensitivity to indicate halogenated hydrocarbons present in concentrations of a few parts per million. It is also an object of the present invention to provide a detector tube sensitive to the halogen derivatives of unsaturated hydrocarbons, and to a detector means in which the dissociation reaction and indication are carried on in separate, but joined tubes.

SUMMARY OF THE INVENTION

The present invention comprises a detector tube having a first and second layer for detecting halogenated hydrocarbons. The first layer of the detector tube dissociates or reacts the halogenated hydrocarbon and second layer detects, by colorimetrically indication, the halogen. While both the first and second layers may be positioned in the same tube, the invention preferably utilizes a second tube for the second layer which is connected to the first just prior to use. By using separate tubes, the shelf life of the active components can be greatly extended.

The material used as the first layer of the present invention preferably comprises a support material or carrier such as silica gel which is impregnated with a hexavalent chromium, sulfuric acid, and an activator compound. Activator compounds found suitable for use in the present invention comprise a compound selected from the group consisting of:

I. 3-, 4- and 5-valent nitrogen compounds, such as alkali nitrates, nitric acid and the like;
II. 5- and 7-valent iodine compounds, such as alkali iodates, alkali periodates, iodine pentoxide, and the like; and
III. 4- and 6-valent selenium compounds, such as alkali selenites, alkali selenates and the like.

Group I nitrogen compounds may be used in a range of from 20 to 150 milligrams per 100 grams of support material and preferably, form 20 to 50 milligrams per 100 grams of support material. Group II materials, on the other hand, are preferably added in an amount of from about 1 to 4 grams per 100 grams of support material. Group II materials are preferably added in an amount from about 2 to 2.5 grams to 100 grams of support material.

Preferably, the support material comprises a silica gel having an apparent bulk density of 400–500 g/l and a grain size of from 0.1 to 0.5 mm and preferably, a grain size of 0.3–0.5 mm. The silica gel is preferably impregnated with hexavalent chromium and sulfuric acid. The activator may be added to the support with the impregnation of either the chromium or the sulfuric acid. For example, the activator can be added to water containing chromium trioxide for impregnation. After drying the impregnated silica gel, sulfuric acid is impregnated therein. Alternatively, the silica gel can be impregnated first with chromium trioxide, and, after drying, impregnated with concentrated sulfuric acid having the selected activator dissolved therein.

PRESENTLY PREFERRED EMBODIMENTS

The presently preferred embodiment of the detection tube of the present invention includes first and second layers wherein the first layer is a reaction media comprising a silica gel impregnated with hexavalent chromium, sulfuric acid and an activator. The activator of the present invention is a compound selected from the group consisting of I. 3-, 4-, or 5-valent nitrogen compounds;
II. 5- or 7-valent iodine compounds; and
III. 4- or 6-valent sodium compounds.

The second layer preferably comprises a silica gel impregnated with a benzidine derivative such as orthotolidine.

While the first and second layers may be positioned in a single tube, the preferred embodiment provides that each layer be positioned within separate tubes which are connected together just prior to usage. By maintaining each layer in a separate tube, increased storage life and stability can be maintained.

Figure 1:
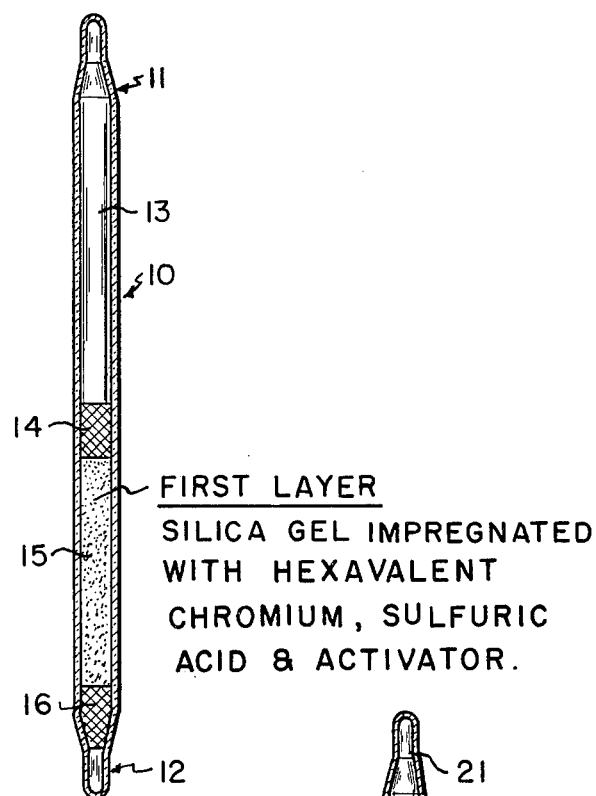
FIGS. 1 and 2 are sectional elevations of a reactor tube and a detecting tube having the first and second layers, respectively, of the present invention.
Figure 2:
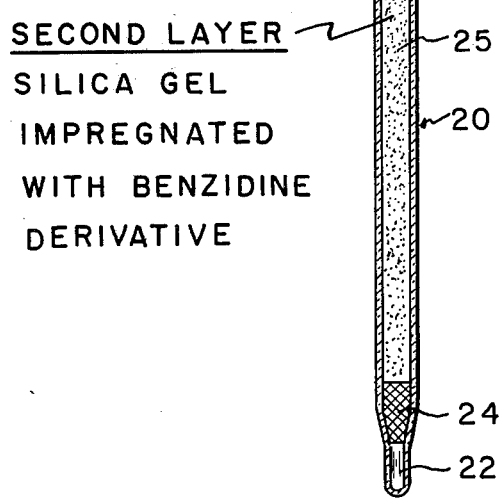

FIGS. 1 and 2 are illustrative of a reactor tube and a detector tube useful in colorimetrically indicating vinyl chloride. With reference to FIG. 1, a reactor tube 10, made preferably of glass, is provided having first and second ends 11 and 12. The inner diameter of tube 10 is approximately 2mm and has a length of about 115 mm. One of the ends is sealed by heating and drawing the end to form the seal prior to placement of the reactor material therein.

As shown in FIG. 1, tube 10 includes an unfilled portion 13 which extends to a first porous plug 14. Positioned between first plug 14 and second plug 16 is first layer 15. After the first and second plugs and first layer have been positioned within tube 10, the other end is heated and drawn to a seal. The first and second plugs restrain the movement of the layer and permit the passage of gas therethrough. These plugs are typically made of glass wool and the like.

With respect to FIG. 2, detector tube 20, preferably of glass and of the same dimensions as reactor tube 10, is shown having first and second ends 21 and 22, one of which is heat drawn to a seal prior to adding the detector material. Tube 20 includes first and second porous plugs 23 and 24 with second layer 25 positioned therebetween. Between first plug 23 and first end 21 is an unfilled portion 26. After second layer 25 has been positioned within tube 20, the other end is heat drawn to form a seal.

Figure 3:
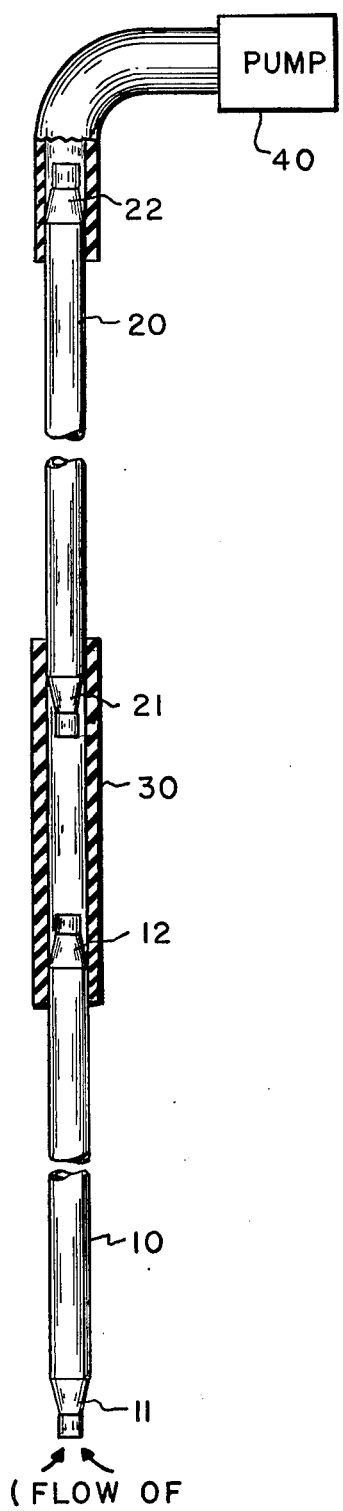
FIG. 3 is an elevation of the detector and reactor tubes connected to a pump.

Tubes 10 and 20 are used to detect vinyl chloride, for example, by breaking off the ends of both tubes. As shown in FIG. 3, second end 12 of reactor tube is inserted in the end of short rubber tube connector 30 and first end 21 of detector tube 20 is inserted into the other end of connected to a calibrated pump 40, which may be, for example, calibrated to sample 700cc, 300cc or 100cc of atmosphere. First end 11 of reactor tube 10 comprises the inlet through which the atmosphere enters the system.

For detection of vinyl chloride first layer 15 preferably comprises silica gel impregnated with sulfuric acid, chromium trioxide and potassium nitrate. Specifically, 2.5 gms of chromium trioxide ($CrO_3$) are added and dissolved in 40cc of water. 100 mgs of silica gel are washed with $HNO_3$ and added to the water with dissolved $CrO_3$. The gel is then dried and heated to about 175° C to obtain a constant weight. To sulfuric acid (32cc) is added 0.1 gm of potassium nitrate (or 0.1cc nitric acid). The hot impregnated chromic acid gel is added to the sulfuric acid with the dissolved potassium nitrate and mixed until free flowing. The gel is then dried (having an orange color) and added to tube 10.

Second layer 25 comprises 100 gms of silica gel impregnated with 50 mgs of tetraphenyl benzidine in 50 ml of water. Second layer 25 was sensitive to 0.2 ppm vinyl chloride with a 700cc sample. Indication is based upon the vinyl chloride reacting with first layer 15 to liberate chlorine and the color reaction of tetraphenyl benzidine impregnated silica gel (white) with chlorine to give quinoidimonium chloride salt (blue).

Some other halogenated hydrocarbon compounds interfere by forming similar stains. The threshold limit concentration using a 700cc sample, for example, for some other halogenated hydrocarbons compared to vinyl chloride (1 ppm) is

| | |
|---|---|
| carbon tetrachloride | 10 ppm - 0% |
| trichloroethylene | 100 ppm > 500% |
| methylene chloride | 500 ppm - 0% |
| ethyl bromide | 200 ppm - 150% |

Testing for vinyl chloride using tubes 10 and 20 is carried out at a temperature greater than 40° F and less than 100° F. Preferably sampling is carried out at a temperature of 70°-80° F. Temperatures below 70° will result in a shortened stain length while temperatures above 80° F will increase the length of stain. Also, it is preferable to sample at 75° F with air at a relative humidity of 50%. Decreased relative humidity will shorten the stain length while increased relative humidity will lengthen the stain. Sampling is preferably not conducted above 90% R.H.

The following examples set forth the presently preferred embodiments of the composition of the present invention comprising a first layer suitable for use in detector tubes.

EXAMPLE I (First Layer)

One hundred grams of silica gel having an apparent bulk density of 400–500 g/l and an apparent grain size of 0.3–0.5 mm was impregnated with 2.5 grms of chromium trioxide and 500 ml of water. After drying to a constant weight, 50 ml of concentrated sulfuric acid, into which was dissolved 50 ml of potassium nitrate, was added to the silica gel. The dried silica gel comprises a first layer suitable for use in the reactor tube.

EXAMPLE II (First Layer)

One hundred grams of silica gel having an apparent bulk density of 400–500 g/l and apparent size of 0.3–0.5 mm was impregnated with 2.5 grs of chromium trioxide and 2 grs of iodine pentoxide in 50 ml of water. The silica gel was dried to a constant weight and 60 ml of concentrated sulfuric acid was added thereto. After drying, the silica gel comprised a first layer suitable for use in reactor tubes 10 of the present invention.

A detector tube comprising a first layer as set forth in Example I was tested with a second layer comprising 100 grs of silica gel impregnated with 50 mgs of orthotolidine dichloride in 50 ml of water dried to a water content of 1–2% by weight. This tube was found to maintain its stability during storage and was highly sensitive to halogenated hydrocarbon compounds. For example, an indication (8mm stain) of 0.2 ppm of vinyl chloride was obtained when 1 liter of testing air was drawn through the tube.

While presently preferred embodiments of the invention have been shown and described with particularity, the invention may be otherwise embodied within the scope of the appended claims.

What is claimed is:
1. A detector means for detecting halogenated hydrocarbons comprising at least one tube having an inlet and outlet port and first and second layers, said first layer positioned adjacent said inlet port and comprising a carrier impregnated with hexavalent chromium, sulfuric acid and an activator compound being selected from the group consisting of 3-, 4-, 5-valent nitrogen compounds, 5-, 7-valent iodine compounds, and 4-, 6-valent selenium compounds; and said second layer being positioned adjacent said outlet port and comprising a carrier impregnated with a benzidine derivative.

2. A detector means as set forth in claim 1 wherein the amount of activator present in the first layer is 20 to 150 mg/100g of carrier for said nitrogen compounds, 1 to 4g/100g of carrier for said iodine compounds, and 2 to 2.5g/100g of carrier for said selenium compounds.

3. A detector means as set forth in claim 1 wherein said first layer is positioned within a first tube and said second layer is positioned within a second tube, each of said first and second tubes having an inlet and an outlet port, and connector means connecting said outlet port of said first tube with the inlet port of said second tube.

4. A detector means as set forth in claim 1 wherein said activator is a compound selected from the group consisting of alkali nitrates, alkali nitrites, nitric acid, alkali iodates, alkali periodates, iodine pentoxide, alkali selenites and alkali selenates.

5. A detector means as set forth in claim 1 wherein each carrier is silica gel.

6. A detector means as set forth in claim 5 wherein said silica gel has an apparent bulk density of from 400 to 500g/l and a grain size of between 0.3 to 0.5 mm.

7. In a detector tube for detecting halogenated hydrocarbons comprising a first reaction layer and a second detecting layer, the improvement comprising a first layer comprising a carrier impregnated with hexavalent chromium, sulfuric acid and an activator, said activator being a compound selected from the group consisting of 3-, 4-, 5-valent nitrogen compounds, 5-, 7-valent iodine compounds, and 4-, 6-valent selenium compounds.

8. The improvement set forth in claim 7, wherein said activator is a compound selected from the group consisting of alkali nitrates, alkali nitrites, nitric acid, alkali iodates, alkali periodates, iodine pentoxide, alkali selenites and alkali selenates.

9. A means for detecting halogenated hydrocarbons comprising
   a. a first tube having an inlet and outlet port and including therein a carrier impregnated with hexavalent chromium, sulfuric acid, and a compound selected from the group consisting of 3-, 4-, 5-valent nitrogen compounds, 5-, 7-valent iodine compounds, and 4-, 6-selenium compounds;
   b. a second tube having an inlet and outlet port and including therein a carrier impregnated with a benzidine derivative; and
   c. means connecting the outlet of said first tube with the inlet of said second tube whereby gas entering the first tube passes through said second tube.

10. Means as set forth in claim 9 wherein the inlet and outlet ports of said first and second tubes are sealed prior to use.

* * * * *